United States Patent [19]

Prabhakaran et al.

[11] Patent Number: 5,227,731
[45] Date of Patent: Jul. 13, 1993

[54] METHOD OF CONTINUOUSLY DETERMINING CRACK LENGTH

[75] Inventors: Ramamurthy Prabhakaran, Virginia Beach; Osvaldo F. Lopez, Newport News, both of Va.

[73] Assignee: The United States of America as represented by the Administrator of the National Aeronautics and Space Administration, Washington, D.C.

[21] Appl. No.: 705,474

[22] Filed: May 24, 1991

[51] Int. Cl.⁵ .................... G01R 27/02; G01N 19/08
[52] U.S. Cl. .................................. 324/718; 324/699; 73/799
[58] Field of Search .............. 324/691, 643, 699, 718, 324/724; 73/768, 774, 799, 826, 834

[56] References Cited

U.S. PATENT DOCUMENTS

| | | | |
|---|---|---|---|
| 2,589,983 | 3/1952 | Blodgett et al. | 73/776 |
| 3,603,142 | 9/1971 | Saylak | 73/799 X |
| 4,255,974 | 3/1981 | Dufrane et al. | 73/799 X |

OTHER PUBLICATIONS

Dally, J. W. and G. A. Panizza. "Conductive Polymers as Fatigue-damage Indicators" *Experimental Mechanics*, Mar. 1972, pp. 124-129.

CDC-2; Crack Detecting Coating; BLH Electronics, Waltham, Mass., Sep. 1977.

Krack-Gage; Drawings, Specifications, Selection Table; Hartrun Corp., St. Augustine, Fla.; pp. 2-6, Jan. 1990.

Crack Detection Gages: Catalog 500, Part A-Strain Gage Listings; Micromeasurements Division, Raleigh, N.C., pp. 76-79, Dec. 1988.

*Primary Examiner*—Jack B. Harvey
*Attorney, Agent, or Firm*—Kevin B. Osborne

[57] ABSTRACT

A crack length sensor is fabricated in a rectangular or other geometrical form from a conductive powder impregnated polymer material. The long edges of the sensor are silver painted on both sides and the sensor is then bonded to a test specimen via an adhesive having sufficient thickness to also serve as an insulator. A lead wire is connected to each of the two outwardly facing silver painted edges. The resistance across the sensor changes continuously as a function of the crack length in the specimen and sensor.

12 Claims, 8 Drawing Sheets

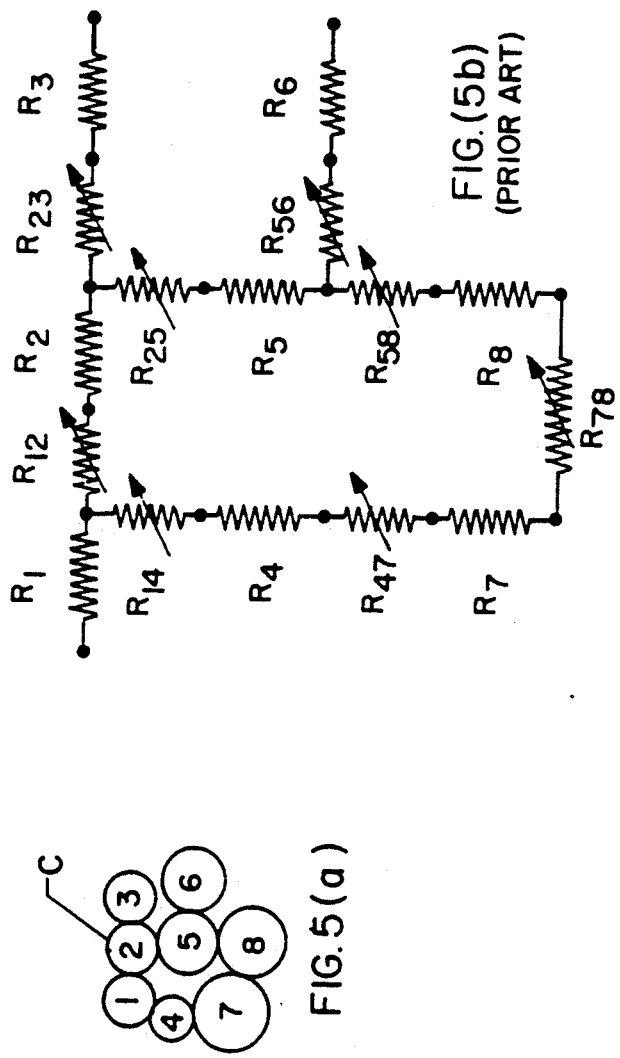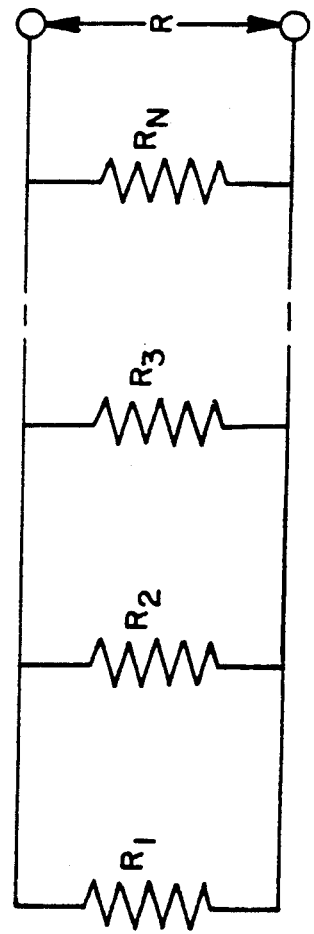
FIG.(5b) (PRIOR ART)
FIG.5(a)
FIG. 6

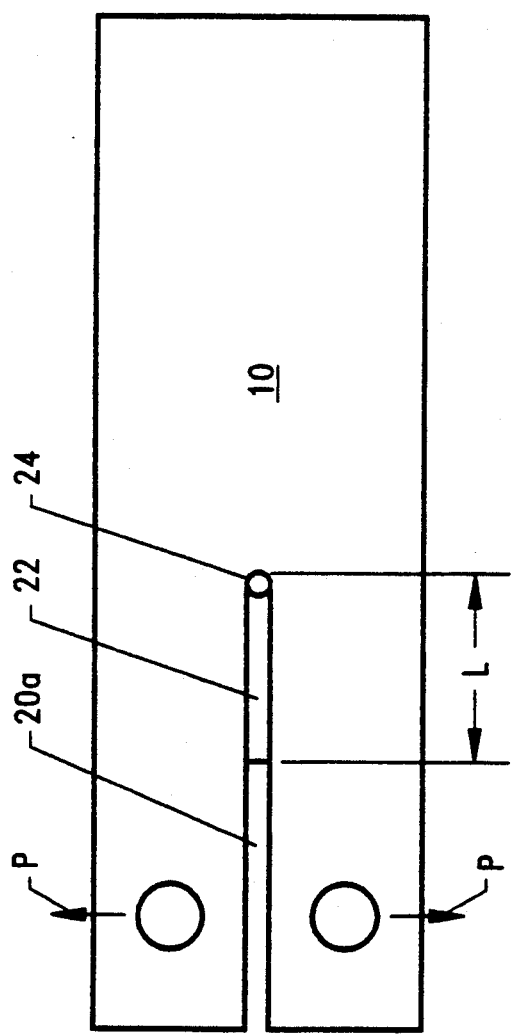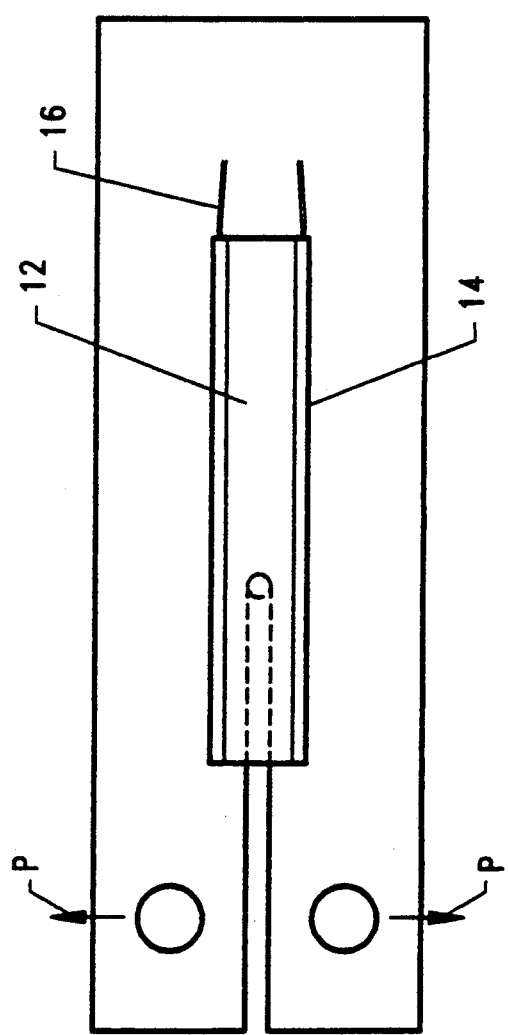

METHOD OF CONTINUOUSLY DETERMINING CRACK LENGTH

ORIGIN OF THE INVENTION

The invention described herein was jointly made in the performance of work under NASA Contract NAS1-18584 and an employee of the United States Government. In accordance with 35 U.S.C. 202, the contractor elected not to retain title.

BACKGROUND OF THE INVENTION

1. Technical Field of the Invention

The present invention relates generally to material testing and more particularly to a sensor for detecting crack lengths.

2. Discussion of the Related Art

Structural defects such as flaws and cracks are formed in materials during the manufacturing process or during subsequent loading. These cracks propagate due to applied loads and can result in catastrophic failure. Two of the broad objectives of improved design methodology are to select tough materials that resist crack formation and crack propagation and to monitor the growth of the crack so that repair or replacement can be accomplished at appropriate intervals. Monitoring may be accomplished by actual measurement or by employing appropriate models.

Techniques for the detection and measurement of cracks depend upon several factors such as the nature of the material, crack size, crack location and the nature of the loading, i.e., static or dynamic loading. Visual inspection, either naked or aided by dye penetrant or magnetic particles; reduction in stiffness; increase in damping; x-ray radiography; holographic interferometry; ultrasonics; acoustic emission; eddy current; potential drop and resonant frequency measurements are some of the methods which have been developed for assessing the crack damage in components and structures. For applications where cracks are well defined and are present on the surface of the component or structure, special gages have been developed. These gages are bondable and give an electrical signal as the output. A crack detection coating, consisting of an epoxy base layer matrix containing micro-capsules filled with an electrically conductive emulsion and a top layer of silver conductive paint, has been marketed under the name "CDC-2" by B.L.H. Electronics of Waltham, Mass. A crack in the base structure propagates into the epoxy layer, rupturing the micro-capsules and causing conduction between the metallic structure and the conducting paint. Various crack detection gages and crack propagation gages incorporating thin metallic filaments are also commercially available from the Micro-Measurements Division of the Measurements Group, Inc. of Raleigh, N.C. A crack in the base structure, on which the gages are bonded, ruptures the gage filaments, resulting in an increase in the total resistance. In a variation of this concept, the crack propagation gage is deposited on the specimen by a silkscreen process using a silver-epoxy resin mixture.

The output from gages that consist of filaments or strands is discontinuous and the resolution depends upon the number of lines per unit length. To overcome this limitation, a bondable foil gage that produces a continuous DC output voltage proportional to the crack length through an indirect potential drop measurement technique has been developed and marketed by the Hartrun Corporation of St. Augustine, Fla. under the name "Krak-gage". The gage, of course, has to be used with the accompanying instrumentation. In the DC potential drop method, a constant direct current is passed through the specimen if it is conducting or through a thin conducting gage bonded to the specimen. The process is usually monitored by measuring the potential difference between two probes placed on either side of the crack. The technique requires that the calibration relationship between crack length and measured potential be determined either by experimental or theoretical means.

Thus, the bondable filamentary gages that do not require special instrumentation do not give a continuous output and the bondable foil gage that gives a continuous output requires special instrumentation. The direct bonding of nonmetallic resistor elements, in the form of a carbon coating, to a structure on which the strain has to be measured, is attributed to A. Bloch as early as 1935. Later this concept was utilized in fabricating gages, with a resistance varying between 15K$\Omega$ and 35K$\Omega$, which could be bonded to a structure for strain measurement. More recently, several types of conducting particle impregnated polymers have been investigated for possible applications as fatigue damage indicators, strain gages and overload indicators, as indicated in the Dally et al reference discussed below.

OBJECTS OF THE INVENTION

It is accordingly an object of the present invention to improve current methods and devices for measuring the length of surface cracks in a material.

It is another object of the present invention to determine crack length in a continuous manner.

It is a further object of the present invention to accomplish the foregoing objects with a bondable gage.

It is another object of the present invention to accomplish the foregoing objects with simple instrumentation.

Additional objects and advantages of the present invention are apparent from the drawings and specification which follows.

SUMMARY OF THE INVENTION

The foregoing and additional objects are obtained by a crack length sensor according to the present invention. The crack length sensor is fabricated in a rectangular or other geometrical form from a conductive powder impregnated polymer material. The long edges of the sensor are silver painted on both sides and the sensor is then bonded to a test specimen via an adhesive having sufficient thickness to also serve as an insulator. A lead wire is connected to each of the two outwardly facing silver painted edges. The resistance across the sensor changes as a function of the crack length in the specimen.

BRIEF DESCRIPTION OF THE DRAWINGS

FIG. 5(a) is a physical model and FIG. 5(b) is a complex electrical model of a particle filled polymer for strain conditions;

FIG. 6 is a simplified electrical model of a carbon-powder impregnated polymer sensor used for determining crack length;

FIGS. 8(a) and 8(b) are top views of a specimen with and without a crack length gage bonded thereto.

DETAILED DESCRIPTION OF THE PREFERRED EMBODIMENT

The present invention originated from an attempt to employ carbon powder impregnated polymeric sensors to measure the normal strains in the adhesive layer of a bonded joint. Although this particular application dealt with the measurement of strains, the potential application of conductive polymers in crack length measurement was recognized and explored. Initially, carbon flakes were dispersed in an epoxy matrix and cast in molds to fabricate gages. While such mixtures exhibited satisfactory conducting properties, they could not be fabricated in very small thicknesses suitable for bonding. Therefore, it was decided to fabricate the gage with a commercially available, carbon powder impregnated PVC sheet material sold by the Mitech Corporation under the tradename Magnex AP-900. While sheets of many thicknesses are available, the smallest available thickness of approximately 0.25 mm was selected. This material exhibited a surface resistivity of approximately $10^4$ ohm/cm$^2$. The sensor may have any suitable geometrical shape. In addition, any suitable conducting powder such as carbon, silver, nickel, iron, etc. may be impregnated in any suitable polymer substrate.

Figure 1:
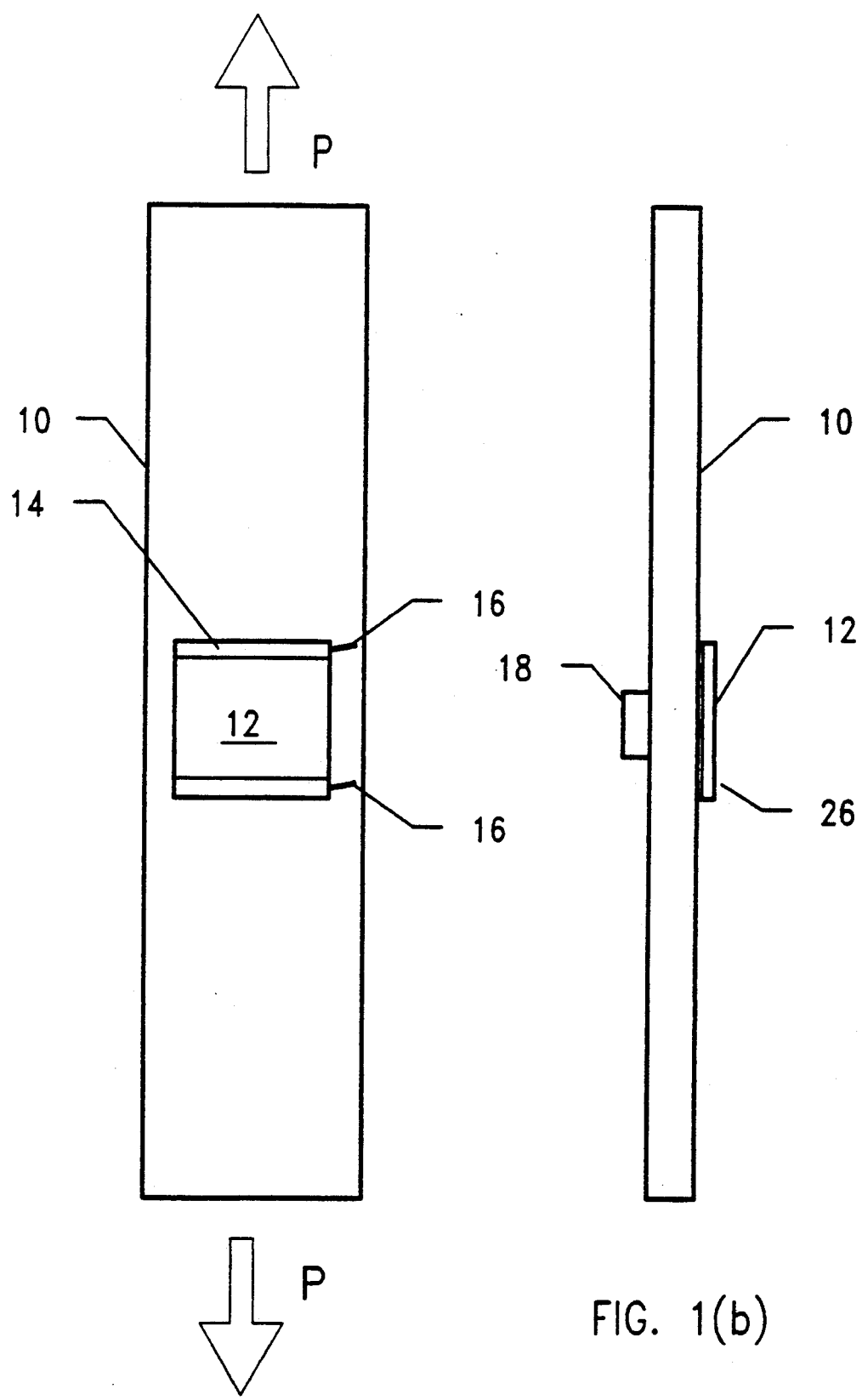
FIG. 1(a) is a top view of a crack length sensor mounted on an uncracked specimen.
FIG. 1(b) is a side view of the embodiment of FIG. 1(a)
Figure 2:
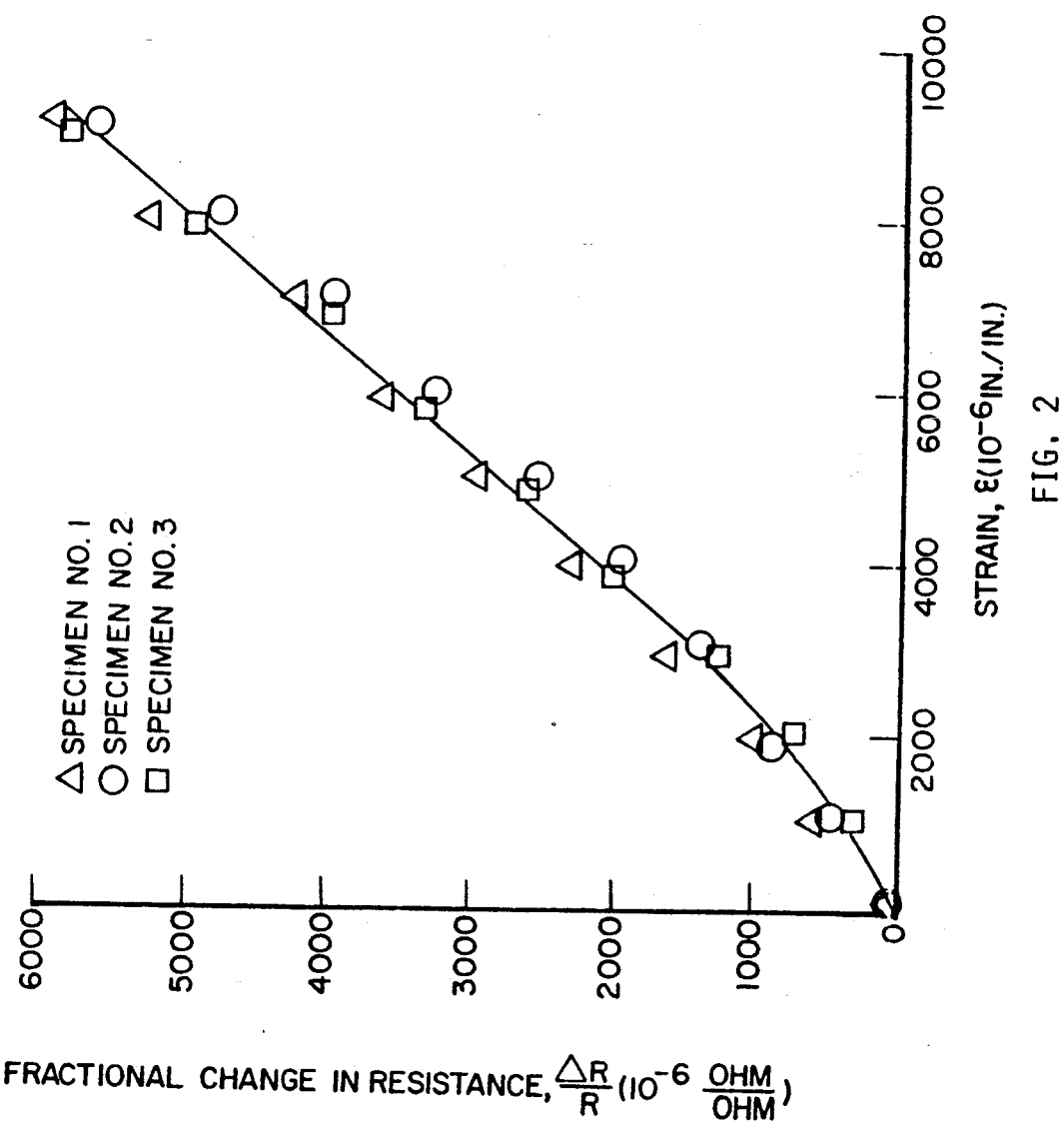
FIG. 2 is a graph showing the resistance change as a function of strain for a carbon-polymer sensor.

To understand the behavior of the gage material, its strain-sensitivity was measured. Referring to FIG. 1(a), a 25 mm × 12 mm sensor 12, cut from a larger sheet of carbon powder-polymer material, was bonded on a 200 mm × 25 mm × 3 mm aluminum specimen 10. These dimensions are by way of example only and are not intended to limit the scope of the present invention in any way. The edges perpendicular to the specimen longitudinal axis were silver painted with paint 14 and lead wires 16 were attached with the silver paint. FIG. 1(b) shows a strain gage 18 mounted on the opposite face of the specimen 10 with the gage longitudinal axis aligned with the specimen longitudinal axis. The specimen 10 was subjected to a gradually increasing tensile load along the longitudinal axis, as indicated by the arrows P, and the electrical resistance of the sensor 12 and the response of strain gage 18 were recorded. The change in electrical resistance, as a fraction of the initial resistance, is shown in FIG. 2 as a function of the strain for three identical tests. It is seen that the repeatability of the test is good and that the response is almost linear, except for some nonlinearity at low strains. The average gage factor for the sensor material is approximately 0.6.

Figure 3:
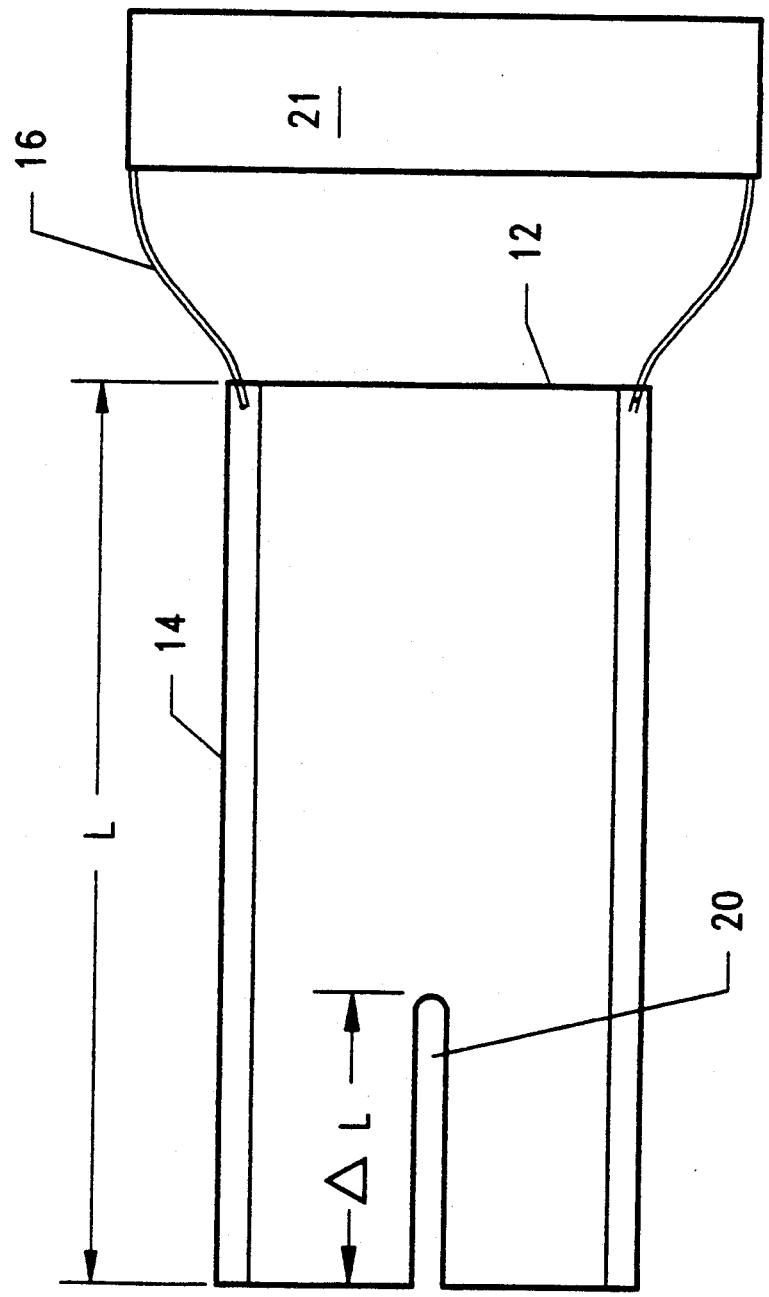
FIG. 3 is a top view of a crack length calibration sensor.

Further tests were conducted to study the response of the sensor material to breaks in the carbon chains. Referring to FIG. 3, in a first series of tests a slit 20 of gradually increasing length ΔL was introduced in rectangular calibration sensors 12 and the electrical resistance was measured with an appropriate resistance measuring device schematically represented by element 21, such as a digital ohm-meter. The calibrations were all 25 mm wide and the long edges were silvered on both faces. Short electrical wires 16 were attached to each sensor at the end with silver paint. The continuous length L of the sensor was varied from 25 mm to 150 mm, in steps of 25 mm. For each length, at least two sensors were tested. The initial resistance R of the sensors was measured and was in the range of 1-10KΩ.

Figure 4:
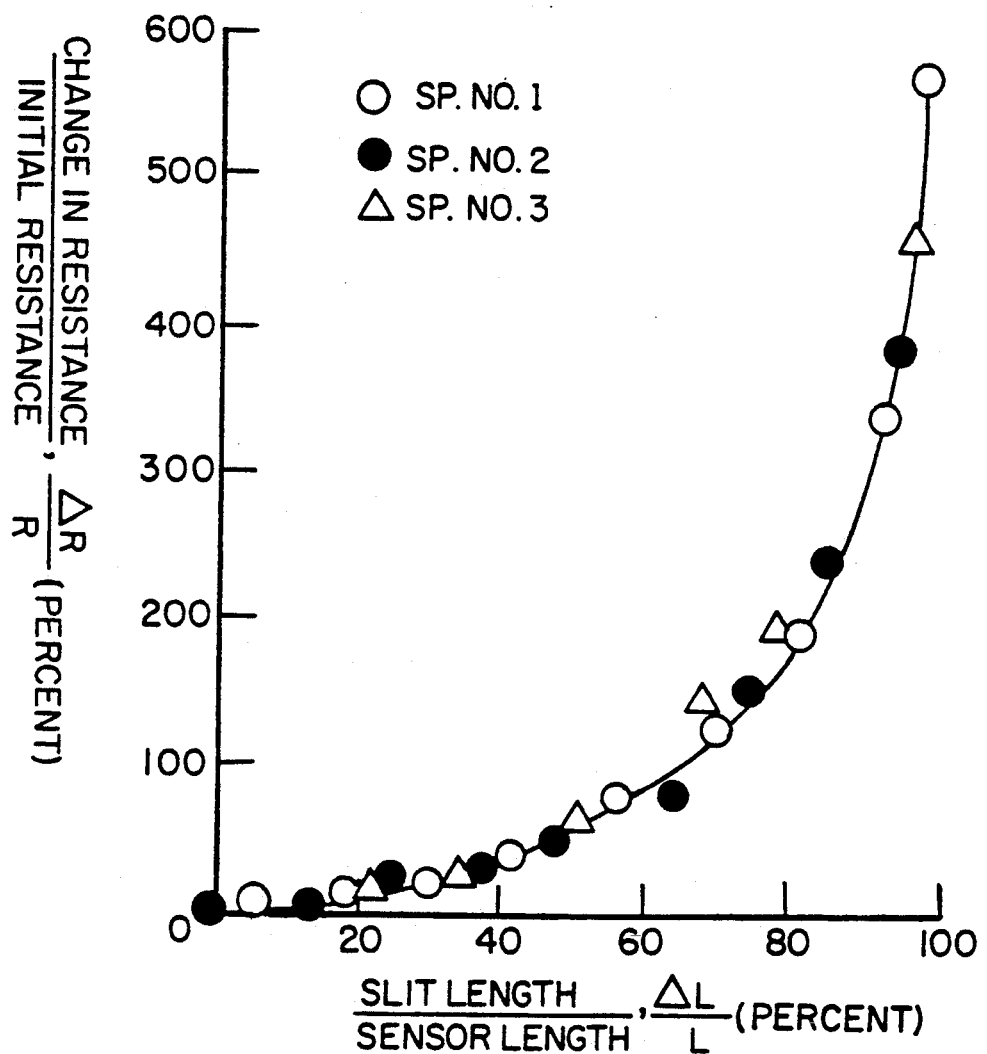
FIG. 4 is a graph of resistance change percent versus crack length change percent for L=25 mm.

The slit 20 was cut in each sensor by a jig-saw parallel to the silvered edges and both the length ΔL of the slit and the resulting electric resistance were measured. The slit, approximately 0.8 mm in width, was lengthened in small steps over the entire length L of each sensor. The slit length ΔL and the resistance were measured after each step. The fractional change in resistance, ΔR/R, was plotted as a function of the ratio of the slit length to the sensor length, ΔL/L, for each sensor. The results for three identical, 25 mm long sensors are shown in FIG. 4. The repeatability of the experimental results is seen to be very good, indicating that the concept of utilizing measured changes in electrical resistance to indicate corresponding length of a geometrical discontinuity such as a slit or crack is feasible.

An attempt was made to predict the change in resistance due to the slit. To accomplish this, the sensor had to be represented by an electrical model. A relatively complex electrical model is discussed in "Conductive Polymers as Fatigue Damage Indicators," by J. W. Dally and G. A. Panizza in *Experimental Mechanics*, Vol. 12(3), pp. 124–9, 1972, and is represented in FIGS. 5(a) and 5(b). The article discusses a graphite-epoxy composite in detail for use as a fatigue damage indicator. The electrical model is applicable to a carbon impregnated polymer. Modifying this two-dimensional model, each carbon particle C is represented by a fixed resistor for its own internal resistance and a variable resister for each point of contact with an adjacent carbon particle. This complex model was simplified for the current investigation because resistance changes due to geometrical discontinuity, and not due to strain, were being measured. The simplified model, shown in FIG. 6, considers all the chains formed by the carbon particles to be arranged in parallel. The effective or equivalent resistance R for the simple model is:

$$R = \frac{R_c}{N} \qquad (1)$$

where $R_1 = R_2 = R_3 = \ldots = R_N = R_c =$ resistance of each carbon particle-chain between the silvered edges and N = total number of chains. When n chains are cut, the fractional change in resistance can be shown to be:

$$\left(\frac{\Delta R}{R}\right)_n = \frac{(n/N)}{1 - (n/N)} \qquad (2)$$

Figure 7:
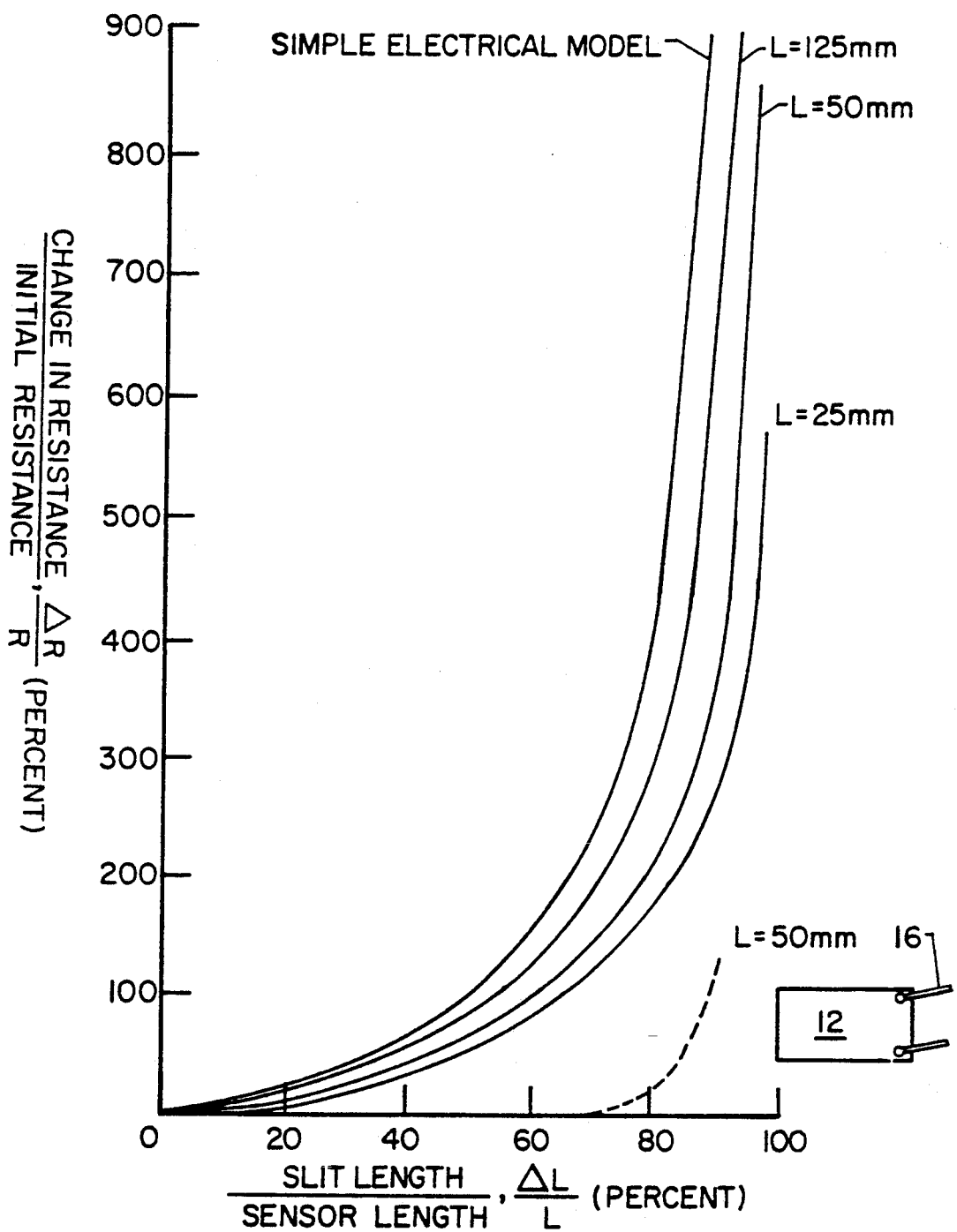
FIG. 7 graphs predicted and actual resistance change percent as a function of length change percent.

If the chains are assumed to be uniformly distributed, the above equation can be rewritten as:

$$\frac{\Delta R}{R} = \frac{(\Delta L/L)}{1 - (\Delta L/L)}, \qquad (3)$$

where ΔL = length of cut or discontinuity and L = length of the edges parallel to the cut. A graphical representation of the above equation is shown in FIG. 7. In this figure, the test results for the sensors with gage lengths of 25 mm, 50 mm, and 125 mm are also shown, as continuous lines. All the sensors had the same width of 25 mm. It is seen that the predicted and measured responses show the same trend and, in general, the measured response approaches the predicted response as the gage length is increased. The dotted curve shows the response of a 50 mm long gage in which short wires were attached at one end with silver paint but the long edges were not silvered; a schematic of this sensor is shown next to the dotted curve. It is clear from FIG. 7 that silvering the opposite edges parallel to the slits has the effect of greatly emphasizing the carbon chains between these edges. Considering the simplicity of the electrical model used for the prediction and the variability due to the nature of the test material, the results were considered very encouraging.

In a second series of tests, sensors 12 cut from the carbon powder dispersed polyvinyl chloride sheet were bonded to aluminum compact tension specimens 10, as shown in FIG. 8(b). The objective of this series of tests was to show that the resistance changes measured for the sensors 12 could be interpreted in terms of crack lengths in the aluminum specimen 10 on which the sensors were bonded. A basic requirement for this calibration was that a crack in the aluminum should extend into the sensor through a bonding adhesive. The faithfulness of this extension depends upon several factors such as the properties of the adhesive, the mechanical properties of the sensor and the loading rate. If the conditions are not optimal, the crack in the sensor can either lead or lag behind the crack in the speciment. In many practical situations, crack length measurements are made under fatigue or impact loading conditions.

In experiments of this type, the crack length in the specimen should be independently measured or controlled. In this test, the crack length in the aluminum specimens was sought to be controlled by machining a groove 22 ahead of a slit 20a in the specimen 10 to reduce the specimen thickness and by drilling a hole 24 at the end of the groove 22, as shown in FIG. 8(a). This procedure was also influenced by the decision to apply static or quasi-static loads, indicated by arrows P, rather than fatigue loads. A possible consequence of this procedure was crack acceleration as the induced crack approached the hole 24.

Three different values of the groove length L were used: 25 mm, 50 mm, and 75 mm. For each length, several specimens were tested. On each specimen, a sensor 12 of approximately 25 mm width and 89 mm length was bonded on the face opposite to the groove 22, with one sensor edge overlapping the slit 20. A room temeprature curing, two-component epoxy cement 26, as shown in FIG. 1(a), was employed for the bonding of sensor 12 to the specimen 10. The adhesive thickness employed exceeded the minimum amount needed for the bonding in order to ensure electrical insulation. The long edges of the sensor were silvered on both faces before bonding and lead wires 16 were attached to the sensor by silver paint 14 after bonding. A short slit of 0.8 mm width was cut in the grooved region of the aluminum specimen and in the overlapping sensor edge to serve as a starter crack. Then the load P was applied via holes 30 in specimen 10 until a crack extended to groove hole 24. At each stage, the sensor resistance was measured via an ohm-meter. A typical sensor response is shown in FIG. 9 for a speciment with L=50 mm.

Figure 9:
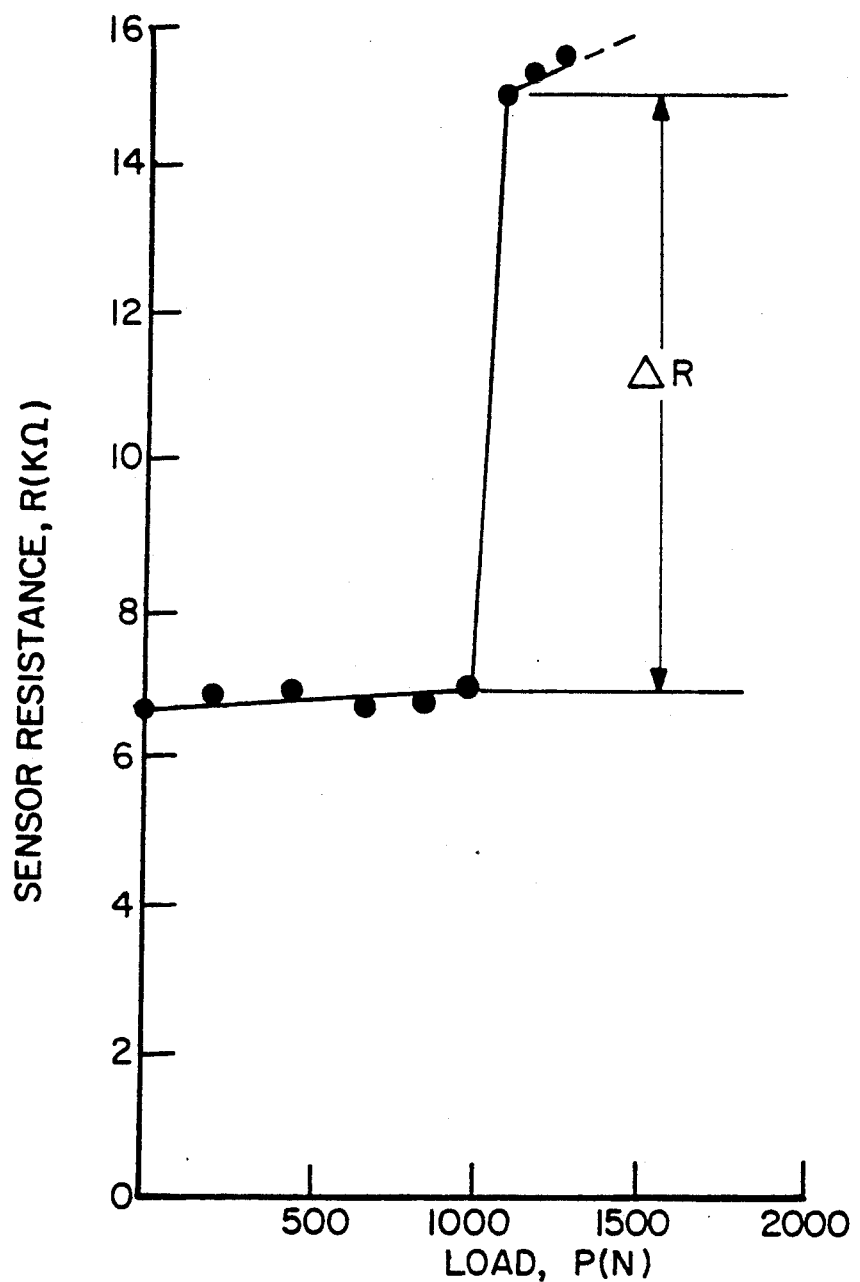
FIG. 9 is a graph of the crack length sensor resistance versus load.

As shown in FIG. 9, the crack gage exhibited an intial resistance of about 6.6KΩ when bonded to an aluminum specimen with a grooved length L of 50 mm. In the intial stages of loading, the resistance increased steadily but by very small amounts due to the strain-sensitivity of the gage. At a load of approximately 1000N, the crack propagated and extended to the hole, resulting in a jump in gage resistance, ΔR, of about 8.3KΩ. Further loading resulted in steady but small increments of resistance. The fractional abrupt change in resistance was interpreted, with the help of a gage calibration curve as shown in FIG. 7, as a crack extension length of 45.7 mm. Typical results from this series of tests are summarized in Table 1.

TABLE 1

| | Crack Extension Test Results | |
|---|---|---|
| L (mm) | Actual Crack Extension (mm) | Measured crack extension (mm) |
| 25 | 22.0 | 21.7 |
| | 22.0 | 20.6 |
| | 22.0 | 23.9 |
| 50 | 47.0 | 45.7 |
| | 47.0 | 52.6 |
| | 47.0 | 46.5 |
| 75 | 72.0 | 73.9 |
| | 72.0 | 76.5 |
| | 72.0 | 74.7 |

It is interesting to note in Table 1 that for all three specimens with L=75 mm, the measurements indicate an overshooting of the crack in the crack gage. This could have been the result of crack acceleration. For the specimens with L=25 mm and L=50 mm, only one of the three specimens showed this behavior.

Thus, the feasibility of using carbon powder impregnated polymeric gages for measuring surface crack extensions in components and structures is shown. The gages are inexpensive and do not require special instrumentation. The results are repeatable and the reported results indicate a maximum error of about 12 percent. The accuracy can be expected to be better with thinner gages and thinner adhesive layers; the matrix for the carbon powder should also be sufficiently brittle. The gage sensitivity can also be improved by optimizing the shape of the gage.

Many improvements, modifications and substitutions will be apparent to the skilled artisan without departing from the spirit and scope of the present invention as described herein and defined in the following claims.

What is claimed is:

1. A method of continuously determining the length of a crack in a specimen comprising the steps of:
    bonding a conducting substrate having a continuous length to the specimen,
    measuring a resistance continuously across the conducting substrate as a crack propagates in the specimen and in the substrate along the length of the substrate; and
    correlating a change in the measured resistance across the conducting substrate with the length of the specimen crack.

2. The method according to claim 1, wherein said measuring step comprises attaching lead wires to opposite edges of the substrate and connecting the lead wires to means for measuring the resistance between the lead wires.

3. The method according to claim 2, wherein the opposite edges are aligned parallel with the direction of an induced crank in the specimen.

4. The method according to claim 2, wherein the lead wires are attached to the substrate via silver paint.

5. The method according to claim 1, further comprising applying silver paint to one side of opposite edges of the substrate, attaching lead wires to the other side of the substrate opposite edges with silver paint after bonding the substrate to the specimen, and connecting the lead wires to means for measuring the resistance between the lead wires.

6. The method according to claim 5, wherein the opposite edges of the substrate are aligned parallel with the direction of an induced crank in the specimen.

7. The method according to claim 1, wherein said bonding step comprises applying an adhesive between the substrate and the specimen.

8. The method according to claim 7, further comprising applying the adhesive in a thickness sufficient to insulate the substrate from the specimen.

9. The method according to claim 1, wherein the conducting substrate is a polymer substrate impregnated with a conducting powder.

10. The method according to claim 9, wherein the conducting powder is selected from the group consisting of carbon, silver, iron and nickle.

11. The method according to claim 1, wherein said correlating step comprises correlating the change in measured resistance with a length of a crack along the length of the conductor substrate, the crack length of the substrate being indicative of the length of the crack in the specimen.

12. The method according to claim 11, further comprising measuring an initial resistance across the conducting substrate prior to the crack propagation, and comparing (1) a ratio of the change in measured resistance to the initial measured resistance of the conducting substrate to (2) previously determined ratios of a change in measured resistance to an initial measured resistance of a reference conducting substrate having similar resistance properties to and the same length as the conducting substrate, each of the previously determined ratios having a corresponding determined reference substrate crack length associated therewith, whereby the crack length to the conducting substrate is determined, whereby the crack length in the underlying specimen is determined.

* * * * *